(12) United States Patent
Heinrich et al.

(10) Patent No.: US 9,949,803 B2
(45) Date of Patent: Apr. 24, 2018

(54) LIGHTING DEVICE FOR A MEDICAL OR DENTAL INSTRUMENT

(71) Applicant: W&H Dentalwerk Bürmoos GmbH, Bürmoos (AT)

(72) Inventors: Christoph Heinrich, Salzburg (AT); Thomas Jindra, Burmoos (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 731 days.

(21) Appl. No.: 14/158,663

(22) Filed: Jan. 17, 2014

(65) Prior Publication Data
US 2014/0134568 A1 May 15, 2014

Related U.S. Application Data

(63) Continuation of application No. PCT/EP2012/064127, filed on Jul. 19, 2013.

(30) Foreign Application Priority Data

Jul. 19, 2011 (EP) .................................. 11174505

(51) Int. Cl.
*A61C 3/00* (2006.01)
*A61B 90/35* (2016.01)
(Continued)

(52) U.S. Cl.
CPC .............. *A61B 90/35* (2016.02); *A61B 90/30* (2016.02); *A61C 1/088* (2013.01);
(Continued)

(58) Field of Classification Search
CPC . A61C 1/008; A61C 17/0202; A61C 17/0217; A61C 17/02; A61B 19/5202;
(Continued)

(56) References Cited

U.S. PATENT DOCUMENTS 3,109,238 A 11/1963 Marks
6,607,384 B1 * 8/2003 Nakanishi .............. A61C 1/088
433/114
(Continued)

FOREIGN PATENT DOCUMENTS

CN 101432102 5/2009
CN 201510366 6/2010
(Continued)

OTHER PUBLICATIONS

International Search Report for PCT/EP/2012/064127 (dated Mar. 25, 2013).

*Primary Examiner* — Heidi M Eide
(74) *Attorney, Agent, or Firm* — Klarquist Sparkman, LLP

(57) ABSTRACT

Medical or dental instruments having a lighting device, manufacturing methods for such instruments and various lighting devices having an optical semiconductor element are described. The lighting devices have, for example, a body, at least one radiation-emitting surface on a radiation-emitting end of the body and at least one fluid channel which is provided in the body and connects at least one opening which is provided on the radiation-emitting end to one or more fluid sources for dispensing fluid. The lighting devices have, for example, a hollow metallic sleeve, a transparent window for emission of electromagnetic radiation and a socket on which at least one optical semiconductor element is arranged. The socket is made of a ceramic, glass ceramic or glass material, and is connected to the hollow metallic sleeve by a material comprising metal and glass.

54 Claims, 4 Drawing Sheets

(51) Int. Cl.
   *A61C 1/08*       (2006.01)
   *A61M 3/02*       (2006.01)
   *A61B 90/30*      (2016.01)
   *A61C 17/02*      (2006.01)

(52) U.S. Cl.
   CPC ...... *A61C 17/0202* (2013.01); *A61C 17/0217* (2013.01); *A61M 3/02* (2013.01); *A61C 17/02* (2013.01); *F04C 2270/0421* (2013.01)

(58) Field of Classification Search
   CPC ... A61B 90/30; A61M 3/02; F04C 2270/0421
   USPC ........................................................ 433/29
   See application file for complete search history.

(56) References Cited

U.S. PATENT DOCUMENTS

2008/0045802 A1* 2/2008 Brandstaetter ....... A61B 1/0607
                                                   600/199
2008/0118890 A1* 5/2008 Knopp ................. A61C 1/0015
                                                   433/104
2008/0166678 A1* 7/2008 Ramot .................... A61B 1/24
                                                   433/29
2011/0070553 A1* 3/2011 Stempfle ................ A61C 1/088
                                                   433/29

FOREIGN PATENT DOCUMENTS

| | | |
|---|---|---|
| CN | 201728231 | 4/2011 |
| DE | 202005020763 | 9/2006 |
| DE | 102007008115 | 8/2008 |
| DE | 102008008535 | 8/2009 |
| EP | 0914809 | 5/1999 |
| EP | 1093765 | 4/2001 |
| EP | 2420198 | 2/2012 |
| JP | 2000316874 | 11/2000 |
| JP | 2001112779 | 4/2001 |
| JP | 2005177501 | 7/2005 |
| JP | 2006004987 | 1/2006 |
| JP | 2011097984 | 5/2011 |
| WO | WO2010/078368 | 7/2010 |

* cited by examiner

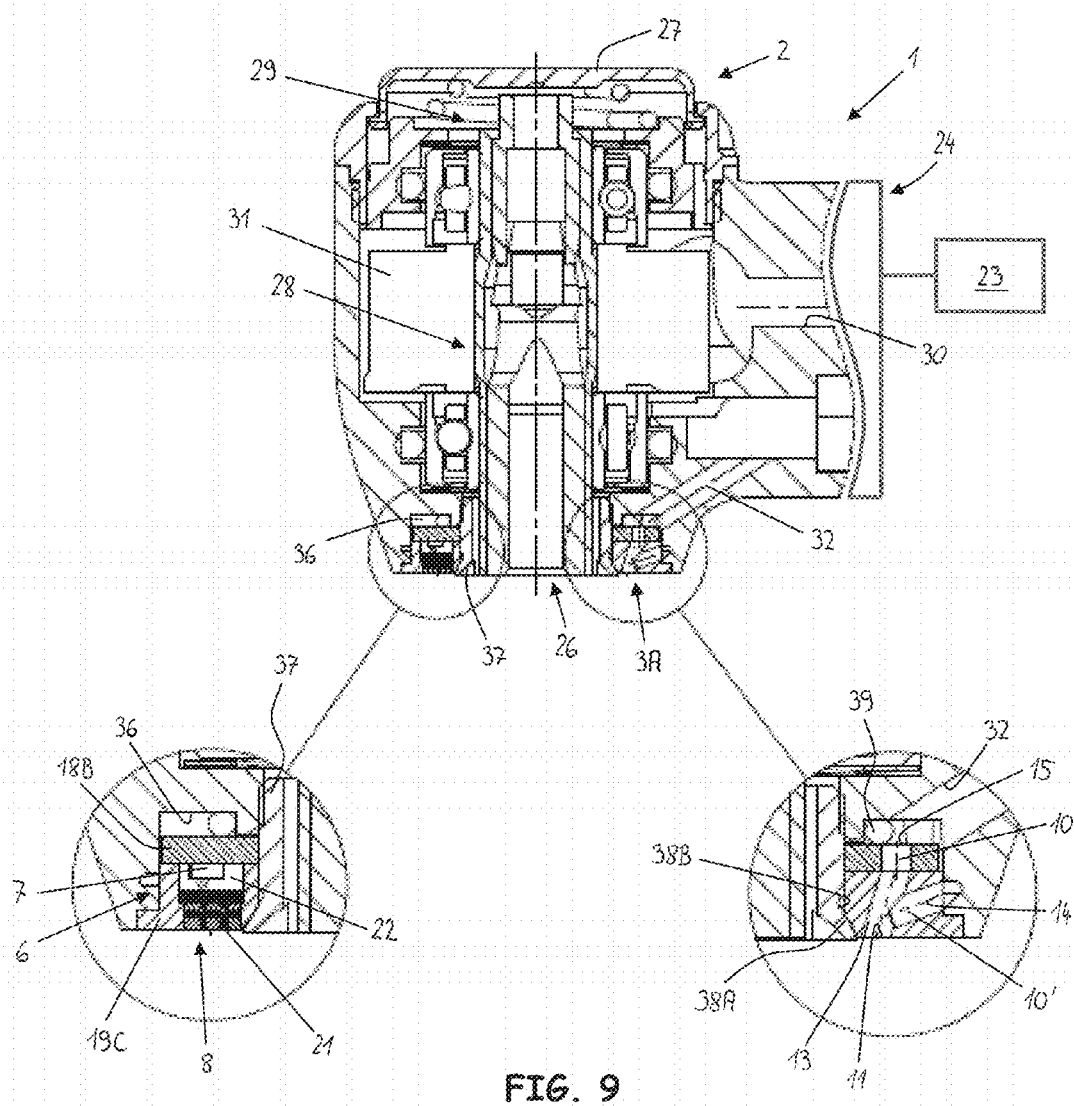

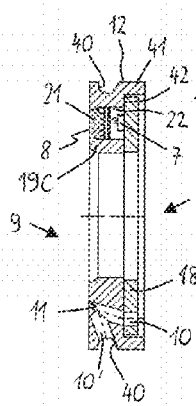
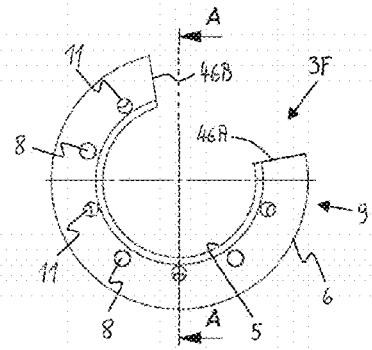
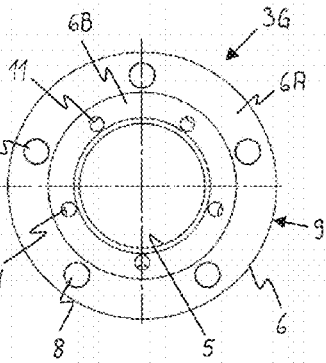
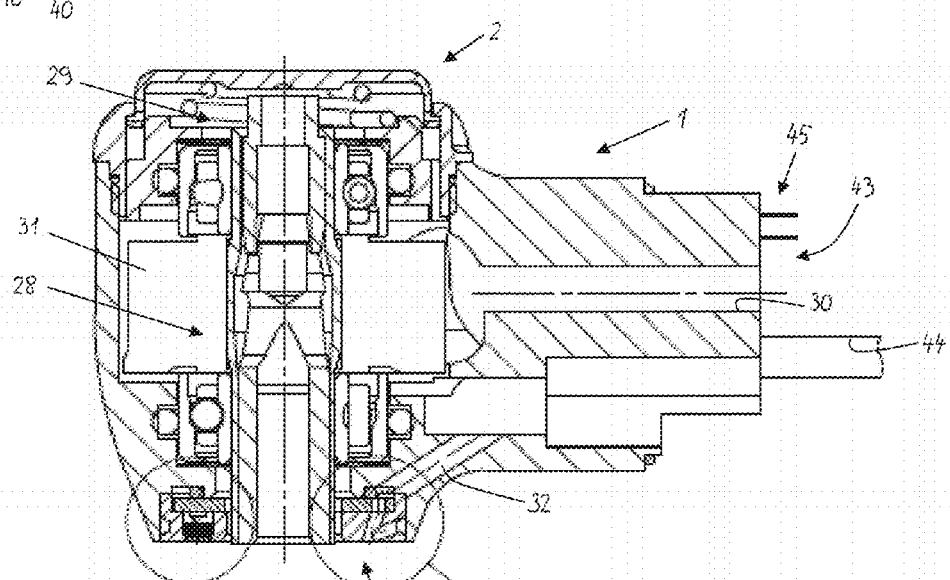

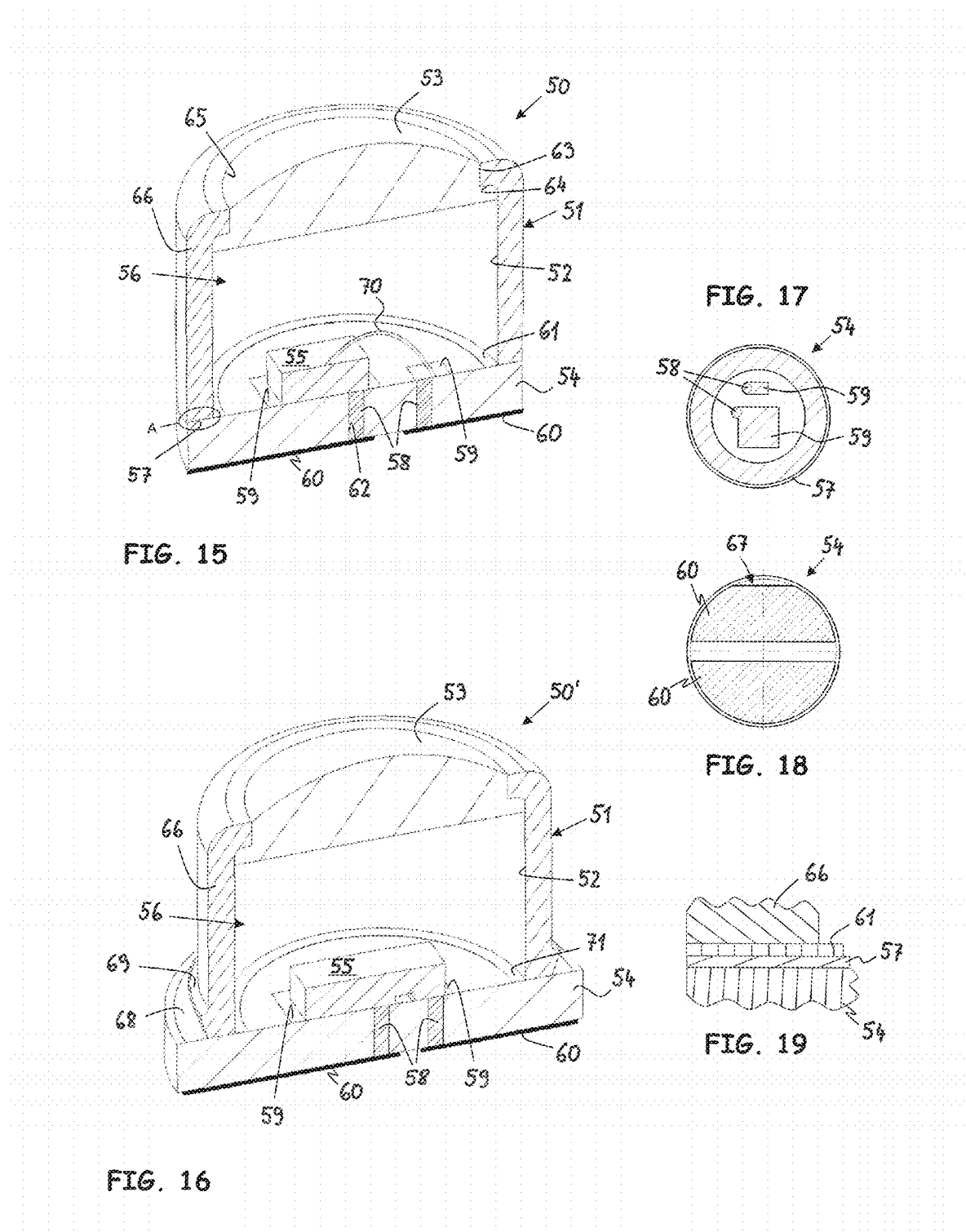

LIGHTING DEVICE FOR A MEDICAL OR DENTAL INSTRUMENT

CROSS REFERENCE TO RELATED APPLICATION

The present application is a continuation of copending International Patent Application No. PCT/EP2012/064127, filed Jul. 19, 2013, and claims priority from pending European Patent Application No. 11174505.5, filed Jul. 19, 2011, which are incorporated herein by reference.

BACKGROUND

Field

The present application relates to a lighting device for a medical or dental instrument, in particular for an instrument head of such an instrument, having at least one semiconductor element which is designed for emission of electromagnetic radiation, in particular radiation in the visible wavelength range.

Description of Prior Art

A lighting device for a medical or dental instrument is known from German Utility Model DE 20 202 020 763 U1, for example. This lighting device comprises a metallic cap with a light-dispensing window and a metallic socket welded to the metallic cap so that an encapsulated interior is formed by the cap and the socket. An optical semiconductor element (LED) for generating light is mounted on the socket and provided in this interior. Two metallic electric contacts penetrate through the socket and are connected to the optical semiconductor element for the purpose of power supply. The two contacts are sealed in glass in the area of the socket. Such a design of the lighting device has proven successful in practice and provides excellent protection of the optical semiconductor element accommodated in the encapsulated interior from aggressive environmental conditions, for example, in cleaning the instrument in a sterilizer and from soiling. However, the encapsulation causes the lighting device to be larger and thus also increases the space required for the lighting device in or on the instrument.

There is thus the problem of creating a lighting device having reduced external dimensions while retaining the well-proven design encompassing the socket, the cap, the light-dispensing window and the encapsulated interior in order to enable or facilitate the arrangement of one or more such lighting devices in or on the medical or dental, instrument or on certain sections or components of an instrument.

An instrument in the form of a dental handpiece with a lighting device is known from the patent application EP 1 093 765 A2, for example. According to one embodiment, the handpiece has a head, on whose bottom side an opening is provided for dispensing of fluid, in particular air or water. In addition, a lighting device with semiconductor elements (LEDs) is provided on the head of the handpiece around an opening to receive a treatment tool. The lighting device with the semiconductor elements is shaped in the form of a horseshoe or a C-shape and thus has two free ends and a clearance between the two free ends. This clearance serves to accommodate the fluid-dispensing opening arranged on the bottom side of the handpiece head as well as an expansion volume of the fluid stream propagating from the fluid-dispensing opening in the form of a cone.

A section from which no radiation is emitted onto the treatment site is created by the clearance between the two free ends of the lighting device, which is a disadvantage, so that a smaller or less well-illuminated region is formed on the treatment site. This is a disadvantage in particular because an essentially uniform illumination to which the user's eye is adjusted is created on the treatment site due to the C-shaped design of the lighting device.

Thus another object is to create a lighting device with at least one semiconductor element for a medical or dental, instrument, in particular for an instrument head of such an instrument or to create a medical or dental, instrument or instrument head with such a lighting device while avoiding the aforementioned disadvantages. The lighting device should in particular be suitable for arranging it around a tool that can be connected to the instrument or to the instrument head and acts on a treatment site or around a receiving opening for such a tool on the instrument or the instrument head to achieve effective irradiation or illumination of the treatment site, and, additionally, to allow an effective supply of one or more treatment fluids to the treatment site.

SUMMARY

According to one embodiment a medical or dental, instrument, preferably a medical or dental handpiece, has a lighting device, wherein the lighting device comprises: a hollow metallic sleeve having a through-bore, a transparent window for dispensing electromagnetic radiation, in particular visible light, and a socket on which at least one optical semiconductor element is arranged, this semiconductor element being designed to emit electromagnetic radiation, in particular visible light, wherein the transparent window and the socket seal off the through-bore of the hollow metallic sleeve in such a way as to form a chamber in which the at least one optical semiconductor element is accommodated, wherein the socket is manufactured from ceramic material or from glass ceramic material or from glass. A material comprising metal and glass and/or a casting material or adhesive material, for example, a silicone resin or an epoxy resin or a silicone or epoxy adhesive is preferably provided for connecting the socket to the hollow metallic sleeve. The material comprising metal and glass is provided for either direct or indirect connection of the socket to the sleeve. In the case of the indirect connection, the material comprising metal and glass is designed in particular as a carrier (material) or as a base (material) or as an adhesion promoter for another material, in particular for a metal alloy or a metal solder.

The lighting device consists of discrete or individual interconnected components, in particular of a hollow metallic sleeve and a socket, and thus retains the known design, which has proven suitable in both application and production. According to the embodiment and in deviation from the teaching known from the prior art, the socket is made of a ceramic material or a glass ceramic material or glass so that a first reduction in the outside diameter or outside cross section of the lighting device is achieved: The document DE 20 2005 020 763 U1 (=DE'763) described above discloses that the sleeve and the socket are manufactured from metal and welded together, to which end a flange labelled as 82 in FIG. 1 of DE'763 is provided on the sleeve and a mating flange is provided on the socket. The flange and the mating flange are needed for welding, in particular resistance welding, among other things, in order to be able to attach the welding electrodes. As shown well in FIG. 1 of DE'763, the flange and the mating flange determine the largest outside diameter of the lighting device.

Using a socket made of a ceramic material or a glass ceramic material or glass, a hollow metallic sleeve and in particular using a material comprising metal and glass and/or a casting material or adhesive material for attaching the socket and the sleeve eliminates the need to provide the socket and the sleeve with a flange and a mating flange so that the outside diameter or outside cross-section of the lighting device are reduced. According to the embodiment the wall thickness of the sleeve wall of the hollow metallic sleeve is sufficient to connect the socket and the sleeve to one another, in particular to connect them together tightly to be able to form a sealed chamber for the at least one optical semiconductor element. The socket may have a round or angular external shape, for example, a rectangular, hexagonal or octagonal shape.

A further reduction in the outside diameter or outside cross section of the lighting device is achieved by a preferred embodiment in which at least one electric contact which is designed for connecting the optical semiconductor element to an electric energy source and which passes through the socket comprises a material comprising metal and glass, in particular a mixture of metal particles and glass particles. It is known from document DE'763 to use metallic pins as electric contacts, which are guided through boreholes in the socket and are provided with a glass seal for fastening, sealing and electrical insulation (see paragraph 61 of document DE'763). The glass seal may be omitted through the use of a socket made of a ceramic material or of a glass ceramic material or of glass and a material comprising metal and glass for the electric contact passing through the socket according to the embodiment, so that the outside diameter or outside cross section of the lighting device is additionally reduced.

According to another embodiment, the lighting device comprises at least one electric surface contact for connecting the optical semiconductor element to an electrical energy source on at least one surface of the socket, wherein the electrical surface contact also includes a material comprising metal and glass.

According to an embodiment, the material comprising metal and glass is designed as a paste material in particular before a heat treatment or sintering treatment. According to another embodiment, the material comprising metal and glass, in particular the paste material, can be or is applied, in particular can be spread to a surface and/or an undercut and/or a borehole and/or a recess of the socket and/or the hollow metallic sleeve. The material comprising metal and glass is preferably applied to the socket prior to the heat treatment or sintering treatment of the socket. The material comprising metal and glass can preferably be connected to the socket or is connected to the socket by heating or sintering. Particularly preferable a tight and/or secure and/or adhering connection to the socket can be formed or is producible by heating, in particular by sintering the material comprising metal and glass, in particular the glass. According to one embodiment, the temperature during the heating or sintering treatment of the socket is approximately 800° C.-1900° C. According to a preferred embodiment the melting point of the glass of the material comprising metal and glass is lower than the temperature of the heating or sintering treatment of the socket, so that the glass melts at least partially and/or bonds at least partially to the socket (caking), so that the tight and/or secure and/or adhering connection of the material comprising metal and glass to the socket is formed, for example.

According to one embodiment, the material comprising metal and glass is designed as a mixture of metal and glass, in particular a paste mixture, in particular as a mixture of metal powder or metal particles and glass powder or glass particles. The mixture additionally preferably contains a solvent, for example, alcohol. According to one embodiment the material comprising metal and glass comprises a metal, in particular a metal powder or granular metal particles in an amount of at least approximately 50 wt %. According to another embodiment, the material comprising metal and glass comprises glass, in particular a glass powder or granular glass particles in an amount of at least approximately 5 wt %. According to one embodiment, the metal or metal powder of the material comprising metal and glass consists of at least one of the following metals: gold, silver, copper, platinum, palladium, tungsten, nickel or molybdenum. According to one embodiment, the glass or glass powder of the material comprising metal and glass comprises, for example, an oxide glass or a silicate glass, for example, silicon dioxide or borosilicate.

As already described above, the material comprising metal and glass is preferably applied to the socket and/or to at least one borehole of the socket. The material comprising metal and glass accommodated in at least one borehole of the socket forms, in particular an electrical connection or contacting through the socket to supply power to the at least one optical semiconductor element. The end or the section of the hollow metallic sleeve that is connected to the socket is preferably also furnished with the material comprising metal and glass. The material comprising metal and glass is applied, for example, by screen printing, preferably by creating a vacuum.

Preferably at least some of the embodiments cited above have the same metal and glass comprising material, in particular being embodied as a paste material at least in some of the embodiments cited above and/or having the same properties and/or the same compositions.

According to one embodiment, the socket is made of a ceramic material, wherein the ceramic material contains, for example, aluminium oxide or aluminium nitride. The socket may of course also comprise other ceramic materials. According to one embodiment, the socket is made of glass, wherein the glass contains an oxide glass or a silicate glass, for example, such as silicon oxide or borosilicate. The socket may of course also comprise other glass materials. According to one embodiment, the hollow metallic sleeve comprises an iron-nickel-cobalt alloy. The hollow metallic sleeve may of course also comprise other metals or metal alloys. According to one embodiment, the transparent window comprises an oxide glass or a silicate glass or a chalcogenide glass, for example, silicon oxide or borosilicate. The transparent window preferably comprises an optical element, for example, a lens or a radiation conductor or is connected to such an optical element. The transparent window is preferably fused in the hollow metallic sleeve or is connected by glass solder to the sleeve.

According to one embodiment, in addition to the optical semiconductor element, at least one other optical component, for example, a reflector or a conversation material for converting the electromagnetic radiation emitted by the optical semiconductor element, in particular for converting the wavelength, is provided in the chamber formed by the hollow metallic sleeve, the socket and the transparent window.

According to one embodiment, the outside diameter of the lighting device is less than approximately 2.5 mm, preferably approximately 2.3-2.1 mm. According to one other embodiment, the height of the lighting device is less than approximately 2.0 mm, preferably approximately 1.8-1.6 mm.

According to one embodiment, the socket, in particular the material comprising metal and glass applied to it, and the hollow metallic sleeve, in particular the material comprising metal and glass applied to it are bonded to one another by a metal alloy, in particular being soldered to one another by a metal solder. The metal alloy comprises, for example, at least one of the following metals: lead, tin, zinc, silver and copper. The metal alloy or the metal solder is preferably in the form of a paste or a discrete solid component before soldering. After applying the metal alloy or the metal solder at least to the socket and arranging the hollow metallic sleeve and the socket, the metal alloy or the metal solder is heated to a temperature above its melting point, so that after cooling, a tight and/or adhering and/or secure connection is formed between the hollow metallic sleeve and the socket. According to this embodiment, the bond between the sleeve and the socket thus comprises two different materials/mixtures of materials, which have in particular different layers or layers arranged one on top of the other or arranged layer-by-layer, namely the material comprising metal and glass and the metal alloy.

According to one embodiment, the at least one electric surface contact comprises multiple layers, wherein a first layer contains in particular the material comprising metal and glass and a second layer applied to the first layer contains a metal. The material comprising metal and glass is preferably applied directly to the socket, in particular before heating or sintering the socket, and the second layer is applied to the first layer, in particular in another workstep after heating or sintering the socket. The second layer comprises in particular gold or a gold-based alloy.

According to one embodiment, the at least one optical semiconductor element is arranged on the at least one surface of the socket with the at least one electric surface contact. According to another embodiment, the at least one surface of the socket with the at least one electric surface contact forms an exterior of the lighting device.

A method for manufacturing a medical or dental instrument, preferably a medical or dental handpiece, having a lighting device comprises the steps:

providing a medical or dental, instrument, preferably a medical or dental, handpiece, providing a lighting device comprising: a hollow metallic sleeve with a through-bore, a transparent window for emission of electromagnetic radiation, in particular visible light, a socket of ceramic material or of a glass ceramic material or glass on which at least one optical semiconductor element is arranged which is designed to emit electromagnetic radiation, in particular visible light, wherein the transparent window and the socket seal the through-bore of the hollow metallic sleeve in such a way as to form a chamber, in which the at least one optical semiconductor element is accommodated, fastening the lighting device in or on the medical or dental, instrument, preferably the medical or dental handpiece.

The socket and the hollow metallic sleeve are preferably bonded by a material comprising metal and glass and/or by a casting material or adhesive material, for example, a silicone or epoxy resin or a silicone or epoxy adhesive. This method comprises in particular at least one additional step of the following steps, wherein the steps are preferably performed in the sequence described below with respect to a manufacturing process for the lighting device:

A material comprising metal and glass is applied to the socket and/or introduced into a borehole in the socket to form or create at least one electric contact for connection of the optical semiconductor element to an electric power source, in particular at least one electric contact which passes through the socket and/or at least one electric surface contact on at least one surface of the socket.

By heating, in particular by sintering, an adhesive and/or tight and/or secure bond between the socket and the material comprising metal and glass is established. If the socket comprises ceramic material, then the socket is preferably reshaped by said heating or sintering, and in particular the final shape and/or size suitable for integration in the lighting device is imparted to the socket.

A second layer containing metal is applied to a first layer containing the material comprising metal and glass, so that the at least one electric contact for connecting the optical semiconductor element to an electric energy source, in particular the surface contact, which comprises the material comprising metal and glass has multiple layers.

The socket, in particular the material comprising metal and glass applied to it and the hollow metallic sleeve, in particular the material comprising metal and glass applied thereto are bonded to one another by a metal alloy, in particular being soldered to one another by a metal solder.

According to another embodiment a lighting device for an instrument head of a medical or dental, instrument, wherein a tool for acting on a treatment site is provided or may be attached to the instrument head, comprises: a receptacle or opening in which the tool can be accommodated, a body surrounding the receptacle or opening, at least one semiconductor element which is provided on the body and is designed for emission of electromagnetic radiation, one or more optically conductive, in particular transparent radiation-emitting surfaces on a radiation-emitting end of the body of the lighting device through which the electromagnetic radiation generated by the at least one semiconductor element can be emitted by the lighting device, and at least one fluid channel provided in the body of the lighting device, connecting at least one opening, which is provided on the radiation-emitting end of the lighting device for dispensing fluid, to one or more fluid sources.

According to an alternative embodiment a lighting device for an instrument head of a medical or dental instrument, wherein a tool for acting on a treatment site is provided on or can be attached to the instrument head comprises: a receptacle or opening in which the tool can be accommodated, a body surrounding the receptacle or opening, at least one semiconductor element provided on the body and designed for emission of electromagnetic radiation, one or more optically-conducting, in particular transparent radiation-emitting surfaces on a surface of the body of the lighting device through which the electromagnetic radiation emitted by the at least one semiconductor element can be emitted by the lighting device and a plurality of openings provided on the body of the lighting device for dispensing a fluid, wherein the openings for dispensing fluid are arranged within the one optically-conducting radiation-emitting surface or adjacent to one or more optically-conducting radiation emission areas or wherein at least one optically-conducting radiation emission area is provided between at least two openings for dispensing fluid.

According to another alternative embodiment a lighting device for an instrument head of a medical or dental instrument, wherein a tool for acting on a treatment site is provided on or can be attached to the instrument head, comprises: a receptacle or opening, in which the tool can be accommodated, a body surrounding the receptacle or opening, said body having a radiation-emitting end with at least one optically-conducting, in particular transparent radiation-emitting area, an instrument-connecting end and a lateral surface extending between the radiation-emitting end and the instrument-connecting end, at least one semiconductor element provided on the body and designed for emission of electromagnetic radiation, so that electromagnetic radiation can be emitted by the at least one optically-conducting radiation-emitting area of the radiation-emitting end, and at least one opening for dispensing fluid, said opening being provided on the radiation-emitting end of the body of the lighting device, so that at least one fluid or one fluid mixture can be dispensed by the radiation-emitting end of the body.

By providing at least one fluid channel or at least one opening for dispensing fluid on the lighting device, uniform emission of radiation and dispensing of fluid from the instrument or the instrument head and in particular a uniform and effective irradiation and a uniform and effective fluid application to the treatment site are achieved in an advantageous manner. Thus a uniform illumination of the treatment site to which the eye of the user can adapt well in particular is achieved advantageously, and reliable cooling of the treatment site and optionally also of the tool is made possible.

The term "instrument" comprises in particular medical or dental devices that can be held in the hand in the particular, for example, straight, gun-shaped, angled or bent handles which are often referred to as contra-angle handpieces in the dental field, parts of handpieces or handles, in particular a head section which can be connected to a detachable handle section, for example, as well as couplings, adaptors, connecting pieces and drive units, for example, electric or pneumatic motors. The term instrument additionally is understood to include both cordless instruments, in particular those with a replaceable or rechargeable energy source, as well as instruments that include a power supply line and a control, regulating and/or supply unit connected thereto.

The term "tool" comprises in particular all the devices which act on a treatment site, for example, drills, saws, dental calculus-removing devices or scaler tips, reamers, files, etc., but also electromagnetic radiation which acts on a treatment site, for example, laser radiation, a particle beam, for example, a particle beam comprising abrasive particles or a fluid jet, for example, a water jet.

The semiconductor element designed for emission of electromagnetic radiation is preferably designed as a light-emitting diode (LED). The radiation emitted by the semiconductor element comprises in particular wavelengths in the range between approximately 380 nm and 780 nm, i.e., essentially visible light. The lighting device is thus preferably designed for illuminating with visible light a treatment site treated with the instrument or instrument head. Alternatively, the semiconductor element is designed to emit radiation for curing of photocuring materials, preferably wavelengths of approximately 440 nm to 480 nm, or radiation for detecting caries or plaque, preferably wavelengths of approximately 390 nm to 420 nm. The lighting device preferably comprises multiple semiconductor elements, which emit radiation with a first and a second different wavelength range, in particular the wavelength ranges defined above, as well as a switching device for optional operation or for optional power supply or for optional radiation emission of at least one semiconductor element which emits the first wavelength range or at least one semiconductor element that emits the second wavelength range.

Especially advantageous embodiments of the embodiments described above are defined in the dependent claims. These preferred embodiments can be implemented in at least one embodiment described above or in two or all of the embodiments described above.

The body of the lighting device or its (outer) lateral surface or outer circumference preferably has a cylindrical shape, in particular a cylindrical outer shape, but may also have other shapes, for example, angular shapes.

The body of the lighting device preferably has a surface or a radiation-emitting end through which the electromagnetic radiation emitted or generated by the at least one semiconductor element can be emitted by the lighting device or in the direction of the treatment site. The surface or the radiation-emitting end preferably has either one or more optically-conducting, in particular transparent radiation-emitting surfaces, preferably optically-conducting for visible light, in particular transparent for visible light radiation-emitting surfaces or the surface or the radiation-emitting end forms a radiation-emitting surface. The surface, the radiation-emitting end or the at least one radiation-emitting surface is preferably round or curved, in particular being curved around the receptacle or opening in which the tool can be accommodated, or it surrounds this receptacle or opening in a ring shape or a circular shape.

The body of the lighting device preferably has an instrument-connecting end. The instrument-connecting end is designed to connect or attach the lighting device to the instrument head or to the instrument. The instrument-connecting end is preferably designed as the transition or interface for transmission of media, for example, electric power or a fluid, between the instrument or the instrument head and the lighting device. Alternatively, the instrument-connecting end is designed as a bearing section or connecting section for media contact elements, for example, for electric contacts for fluid channels or for fluid lines.

The (outer) lateral surface of the body preferably extends between the radiation-emitting end and the instrument-connecting end of the body. The radiation-emitting end and the instrument-connecting end or the surfaces of the body which form the radiation-emitting end and the instrument-connecting end are especially preferably arranged to be essentially parallel to one another.

The opening in the lighting device in which the tool can be accommodated preferably has a round or cylindrical shape, preferably a round or cylindrical inside wall, but it may also have other shapes, for example, angular shapes.

The (outer) lateral surface of the body of the lighting device preferably forms a closed exterior circumference, in particular having a ring-shaped or polygonal cross section. The (outer) lateral surface is thus continuous or not interrupted and does not have a free end. The at least one fluid channel which in particular connects at least one opening which is provided on the lighting device for dispensing fluid to one or more fluid sources, and/or the one or more optically-conducting radiation-emitting surfaces and/or the at least one opening for dispensing fluid and/or the at least one semiconductor element and/or a mixing chamber for mixing several fluids is/are preferably arranged inside the (outer) lateral surface or its exterior circumference for the sake of a compact design of the lighting device. The at least one fluid channel and/or the one or more optically-conducting radiation-emitting surfaces and/or the at least one opening for dispensing fluid and/or the at least one semiconductor element and/or a mixing chamber for mixing several fluids is/are especially preferably arranged between the (outer) lateral surface and the receptacle or the opening in which the tool can be accommodated.

The (outer) lateral surface extends from the instrument-connecting end of the body to one of the following elements: a radiation-emitting end of the body, a surface of the body having one or more optically-conducting radiation-emitting surface(s), the radiation-emitting end.

Multiple fluid channels are preferably provided in the lighting device or in the body of the lighting device to be able to supply different fluids, for example, to the lighting device or to the treatment site, said fluid being in particular a gaseous fluid such as air and a liquid fluid such as water or an aqueous solution. Alternatively, same fluids may be conveyed in the multiple fluid channels but having different properties, for example, different temperatures, different concentrations, different pressures, different volume flows, etc. The multiple fluid channels may preferably be connected or connectable to different fluid sources.

The multiple fluid channels especially preferably open into a joint fluid mixing chamber in the lighting device or they combine to form a joint fluid mixing chamber, wherein the fluid mixing chamber is connected to the at least one opening for dispensing fluid. Thus fluid mixtures, for example, an air-water mixture, can advantageously be dispensed through the at least one opening for dispensing fluid.

The at least one opening for dispensing fluid may preferably be designed as a nozzle or as a nozzle opening or may comprise a nozzle or nozzle opening.

Multiple fluid channels are preferably provided in the lighting device or in the body of the lighting device, wherein at least one fluid channel has an opening for connection to a fluid channel on the (outer) lateral surface or on the exterior circumference of the body of the lighting device and at least one fluid channel has an opening for connection to a fluid source on an instrument-connecting end of the body of the lighting device. This advantageously achieves a particularly good mixing of the fluids conveyed in the individual fluid channels, in particular when the fluid channels are combined.

The at least one fluid channel of the lighting device and/or the at least one opening for dispensing fluid of the lighting device are preferably connected or connectable to one or more fluid sources by means of lines and/or channels in the instrument or in the instrument head.

The lighting device preferably has multiple optically-conducting, preferably transparent radiation-emitting surfaces, in particular ones that are optically-conducting for visible light, and has multiple openings for dispensing fluid wherein at least one radiation-emitting surface is arranged between two openings for dispensing fluid. Thus an especially tight, uniform and effective illumination of and fluid application to the treatment site are achieved in an advantageous manner. Preferably the number of radiation-emitting surfaces provided is between three and nine, in particular five. Preferably between three and nine, in particular five openings are provided for dispensing fluid.

The number of openings for dispensing fluid and the number of radiation-emitting surfaces are either the same or different. The number of openings for dispensing fluid is greater than the number of radiation-emitting surfaces according to one embodiment. According to an alternative embodiment, the number of radiation-emitting surfaces is greater than the number of openings for dispensing fluid.

According to one embodiment, one radiation-emitting surface is provided between two openings for dispensing fluid. According to an alternative embodiment, multiple radiation-emitting surfaces are provided between two openings for dispensing fluid. According to another embodiment, one opening for dispensing fluid is provided between two radiation-emitting sources. According to another embodiment, multiple openings for dispensing fluid are provided between two radiation-emitting surfaces. According to one embodiment, the openings for dispensing fluid and the radiation-emitting surfaces are arranged in alternation.

According to one embodiment, the at least one opening for dispensing fluid and the at least one radiation-emitting surface are essentially the same distances away from the opening in which the tool can be accommodated or the same distance away from a central axis of this opening. According to an alternative embodiment, the at least one opening for dispensing fluid and the at least one radiation-emitting surface are different distances away from the receptacle or opening in which the tool can be accommodated or they are different distances away from a central axis of this receptacle or opening. According to one embodiment, the at least one opening for dispensing fluid is arranged closer to the opening in which the tool can be accommodated or to a central axis of this opening than the at least one radiation-emitting surface. According to one alternative embodiment, the at least one radiation-emitting surface is arranged closer to the opening in which the tool can be accommodated or to a central axis of this opening than the at least one opening for dispensing fluid.

According to one embodiment, the opening for dispensing fluid and the at least one radiation-emitting surface are arranged side by side, in particular directly adjacent to one another. According to an alternative embodiment, the opening for dispensing fluid is arranged inside a radiation-emitting surface or the opening for dispensing fluid is surrounded by a radiation-emitting surface. According to another embodiment, the opening for dispensing fluid and the radiation-emitting surface are spaced a distance apart from one another, in particular spaced a distance apart by a region which does not emit any electromagnetic radiation, in particular does not emit any visible electromagnetic radiation and does not dispense any fluid.

The lighting device is preferably designed as a ring light or as a ring-shaped lighting device in which a plurality of semiconductor elements designed for emitting electromagnetic radiation or the one or more radiation-emitting surfaces are arranged essentially in a ring pattern around the tool that can be connected to the instrument head or to the instrument or around the tool receptacle opening of the instrument head or of the instrument or around the tool holder of the instrument head or of the instrument or around the opening of the lighting device in which the tool can be accommodated. The openings are also especially preferably arranged in a ring around at least one of the aforementioned elements.

The lighting device is preferably provided with a plurality of semiconductor elements connected electrically in series through an electric conductor. Thus only two electric contacts are to be provided advantageously for the electric power supply to the semiconductor elements on the outside or the surface of the lighting device. The electric conductor is designed, for example, as a metallic printed conductor or as a metallic wire. The electric conductor is especially preferably arranged at a distance from the at least one fluid channel provided in the body of the lighting device, in particular at a distance from a fluid channel carrying a liquid. In particular an electrically insulating material, for example, a ceramic material, is provided between the electric conductor and the fluid channel. According to an alternative embodiment, at least two semiconductor elements are connected electrically in parallel.

The lighting device is preferably constructed of multiple layers, in particular multiple layers of different materials. The materials of which one or more of the layers are constructed include, for example, glass, plastic, ceramic or metal.

The glass and/or plastic is/are preferably used for optically conducting the electromagnetic radiation emitted by the at least one semiconductor element through the lighting device and/or towards the at least one radiation-emitting surface of the lighting device. The at least one radiation-emitting surface or at least a portion of the radiation-emitting end of the lighting device or the layer forming a radiation-emitting surface or at least a part of the radiation-emitting end is especially preferably made of glass or plastic. The at least one semiconductor element especially preferably emits visible radiation, and the glass and/or plastic which optically conducts the visible radiation is especially preferably transparent for visible radiation.

Preferably those layer(s), in which the at least one semiconductor element and/or an electric conductor for supplying electric power to the at least one semiconductor element is/are provided, comprise(s) a ceramic material and/or plastic. The layer that contains an electric conductor especially preferably consists of at least two ceramic partial layers, between which the electric conductor is arranged. The conductor arranged between the ceramic partial layers especially preferably does not have any electrically insulating outer jacket or an electrical external insulation. The ceramic material comprises aluminium oxide ceramics, silicon nitride ceramics or aluminium nitride ceramics, for example.

Preferably at least one of the layers comprises metallic material and/or plastic and/or glass, in particular the layer which forms the radiation-emitting end of the lighting device or the layer on which the at least one optically-conducting radiation-emitting surface is provided. The metallic material comprises steel, for example. The plastic comprises polymethyl methacrylate (PMMA), for example.

An embodiment of a lighting device comprises a ceramic layer on which the at least one semiconductor element and/or the electric conductor for supplying the power to at least one semiconductor element is/are provided, and a metallic layer connected to the ceramic layer, wherein at least one optical conductor of glass and/or at least one radiation-emitting surface of glass is/are arranged in the metallic layer for conducting the electromagnetic radiation, in particular visible radiation emitted by the semiconductor element. The glass is preferably fused in the metallic layer.

An alternative embodiment of a lighting device comprises a ceramic layer on which the at least one semiconductor element and/or the electric conductor for supplying power to the at least one semiconductor element is/are provided and a glass layer connected to the ceramic layer for conducting the electromagnetic radiation, in particular visible radiation emitted by the semiconductor element. This embodiment does not have a metallic layer.

Another embodiment of a lighting device comprises a first metallic layer on which the at least one semiconductor element and/or the electric conductor for supplying power to the at least one semiconductor element is/are provided, optionally separated from the metallic layer by an electric insulation medium and a second metallic layer connected to the first metallic layer in which at least one optical conductor of glass and/or at least one radiation-emitting surface of glass is/are arranged or a glass layer connected thereto as described above.

The lighting device preferably has a plurality of semiconductor elements, wherein a separate optical radiation conductor is allocated to each semiconductor element and is arranged in such a way that it conducts the electromagnetic radiation emitted by the semiconductor elements in the direction of the radiation-emitting end of the lighting device or in the direction of the at least one optically-conducting radiation-emitting surface. The radiation conductors extend, for example, from the semiconductor elements in the direction of the radiation-emitting end or the radiation-emitting surface. To further improve the transmission of radiation/light, the radiation conductors may preferably be coated. At least one end of a radiation conductor especially preferably forms at least a portion of the radiation-emitting surface of the lighting device or at least a portion of the radiation-emitting end of the lighting device. The radiation conductors comprise, for example, a glass body, glass rod, glass fibre body, glass fibre rod, plastic body or plastic rod. The optical radiation conductors are especially preferably spaced a distance apart from one another, in particular being separated from one another by a material which does not emit any electromagnetic radiation, in particular no visible electromagnetic radiation or is not transparent, in particular not being transparent for light.

The at least one semiconductor element is preferably arranged in a chamber, in particular a chamber that is hermetically sealed, in the body of the lighting device. The chamber is preferably hermetically sealed in such a way that no particles and/or water vapour and/or liquids can enter the chamber. The chamber is especially preferably hermetically sealed so that it resists multiple cleaning or sterilization operations so that media used in these operations such as cleaning agents or water vapour do not enter the chamber. Preferably at least a portion of the chamber or of the chamber wall surrounding the interior of the chamber is formed by a material which is transparent for the radiation emitted by the semiconductor element and/or which conducts this radiation.

Preferably the chamber or the chamber wall surrounding the interior of the chamber is formed by a plurality of layers of the lighting device which are connected to one another, for example, by melting, fusing, soldering, welding, adhesive bonding, etc. According to one embodiment, the chamber wall is formed by a ceramic layer and a metal layer connected or bonded thereto. An optical radiation conductor which in particular also forms a part of the chamber wall is especially preferably arranged in the metal layer. According to another embodiment, the chamber wall is formed by a ceramic layer and a glass layer bonded to it. According to another embodiment, the chamber wall is formed by a ceramic layer, a metal layer and a glass layer, which are connected or joined together.

In addition to the semiconductor element, at least one additional component is preferably provided in the chamber. According to one embodiment, the additional component comprises an element for converting the wavelength of the radiation emitted by the semiconductor element, for example, a converter, a conversion film or a conversion paste. According to another embodiment, the additional component comprises an electric conductor for supplying the semiconductor element with electric power. According to another embodiment, the additional component comprises an optical element, for example, a reflector, in particular for deflecting the radiation emitted by the semiconductor element in the direction of the radiation-emitting surface and/or a lens for concentrating the radiation emitted by the semiconductor element and/or an optical filter.

An optical radiation conductor which is arranged in such a way that it conducts the electromagnet radiation emitted by the semiconductor elements in the direction of the radiation-emitting end of the lighting device or in the direction of the at least one optically-conducting radiation-emitting surface (as described above in particular) is preferably connected to the chamber, in particular a chamber that is hermetically sealed. Alternatively, the optical radiation conductor or a surface of the optical radiation conductor forms a part of the chamber wall enclosing the interior of the chamber.

The lighting device preferably comprises a control unit for alternating emission of the electromagnetic radiation and dispensing of the fluid from the radiation-emitting end of the lighting device. According to one embodiment, the control unit is designed to emit in alternation one or more radiation pulses and then a fluid pulse from the lighting device, following one another essentially chronologically. According to a preferred alternative embodiment, the control unit is designed to alternately emit one or more fluid pulses and then a radiation pulse from the lighting device, these pulses following one another essentially chronologically.

The control unit preferably comprises one or more control or actuating elements acting on the light-emitting device or on the cooling media-emitting device and in particular a microcontroller connected thereto for controlling the control elements or actuator elements. The control unit especially preferably has a control valve arranged in a media line of a cooling medium, in particular a solenoid valve which can be triggered periodically by the microcontroller for opening or closing by means of control signals. The pulse rate of the control signals or of the control valve and thus also the dispensing of cooling medium amounts to at least approximately 25 Hz, preferably more than approximately 40 Hz, especially preferably approximately 75 Hz.

The control unit preferably also has an electric or electronic switching element for pulsed power supply (supply of electric current) to the at least one semiconductor element. The pulse rate of the lighting device is preferably above the flicker frequency of the human eye and amounts to at least approximately 25 Hz, especially preferably more than approximately 50 Hz, so that for the user there is the impression of a continuous emission of light.

The lighting device is preferably detachably connectable to the medical or dental, instrument or instrument head. The detachable connection is accomplished, for example, through a plug, clamp or screw connection. A stop, for example, a flange designed to contact an opposing stop on the instrument head as soon as the lighting device reaches its predetermined position on the instrument head is preferably provided on the lighting device.

A receptacle, for example, an undercut is preferably provided on the instrument head, so that the lighting device can be accommodated there, in particular detachably. The receptacle is preferably designed to transfer fluid to the lighting device. This receptacle is especially preferably connected to at least one fluid line of the instrument head or of the instrument or a fluid line opens into the receptacle so that fluid can be conveyed from a fluid source through the fluid line and via or through the receptacle to the lighting device or to the at least one fluid channel of the lighting device or to the fluid-dispensing opening of the lighting device. Alternatively or additionally, at least a portion of the receptacle serves as a fluid channel which supplies a fluid to the lighting device or at least a portion of the receptacle together with the lighting device, for example, a recess in the lighting device, forms at least a section of the fluid channel of the lighting device.

According to one embodiment, the lighting device is electrically connected to a generator arranged in the medical or dental instrument so that the lighting device, in particular the at least one semiconductor element can be supplied with electric power generated by the generator. To generate the electric power preferably the generator is driven by a drive element of the instrument which is configured to induce a movement to the tool-holding device or to a tool that can be connected to the instrument, for example, by a drive shaft. Alternatively, the generator can be driven by a fluid, in particular by a drive fluid for the tool-holding device or a tool that can be connected to the instrument.

An electric or electronic control circuit or switching circuit is preferably allocated to the lighting device or is provided in the medical or dental instrument, wherein said electric or electronic control circuit or switching circuit is configured to adjust at least one parameter of the electric power supply for the at least one semiconductor element, in particular the electric voltage. Alternatively or additionally, the brightness of the radiation emitted by the semiconductor element is adjustable through the control circuit or switching circuit, for example, or one of the plurality of semiconductor elements having a certain property, for example, having a specific wavelength range as already described above can be operated or supplied with power.

These and other embodiments will be described below with reference to the following drawings.

BRIEF DESCRIPTION OF THE DRAWINGS

FIG. 8 shows an alternative embodiment of a radiation-emitting end of a lighting device having at least one semiconductor element, wherein the radiation-emitting end has a radiation-emitting surface in which a plurality of openings are arranged for dispensing fluid.

FIG. 9 shows an embodiment of an instrument head or contra-angle handpiece head with a lighting device connected detachably thereto, which has at least one semiconductor element and at least one opening for dispensing fluid as well as, in enlarged details, a semiconductor element of the lighting device and a fluid channel of the lighting device.

FIG. 10 shows an alternative embodiment of a lighting device with a ring channel for a fluid on the (outer) lateral surface.

FIG. 11 shows an alternative embodiment of an instrument head or contra-angle handpiece head with a lighting device indetachably connected thereto.

FIG. 12 shows an alternative embodiment of a lighting device, whose body is made of synthetic resin, in which the at least one semiconductor element is cast.

FIG. 13 shows an alternative embodiment of a lighting device having two free ends.

FIG. 14 shows an alternative embodiment of a lighting device whose body consists of two partial rings.

FIGS. 15 and 16 show two embodiments of lighting devices whose sockets made of ceramic material or of glass ceramic material or of glass are connected to hollow metallic sleeves by a material comprising metal and glass.

FIGS. 17 and 18 show the top side and the bottom side of a socket of ceramic material or of glass ceramic material or of glass of a lighting device as well as the electric contacts provided thereon.

FIG. 19 shows an enlargement of the detail labelled as A in FIG. 15.

DETAILED DESCRIPTION

Figure 1:
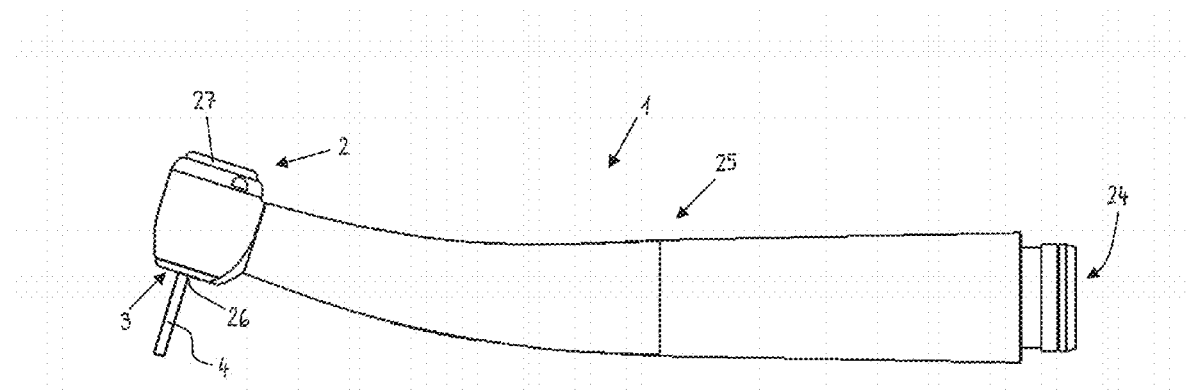
FIG. 1 shows an embodiment of a medical or dental, instrument with a lighting device having at least one semiconductor element for emission of electromagnetic radiation, in particular visible radiation and at least one fluid channel, which is provided in the lighting device and connects at least one opening, which is provided on the radiation-emitting end of the lighting device for dispensing fluid, to one or more fluid sources.

The medical or dental, instrument 1 shown in FIGS. 1 and 9 is designed as an elongated tubular instrument 1 or handpiece which has at one end a connection 24 for detachable connection, for example, to a control device, a drive unit, a power source and/or a fluid source, in particular a water and/or compressed air source. The instrument 1 comprises a handle part 25, which is bent or has two sections arranged at an angle to one another and also has an instrument head 2 connected to the former. A tool opening 26 is provided on the instrument head 2, wherein a tool 4 for acting on a treatment site can be introduced detachably into the instrument head 2 through this tool opening 26. A detachable tool-mounting device 28, for example, a chuck, is arranged in the instrument head 2, securing the tool 4 detachably on the instrument head 2. The tool opening 26 is arranged on the side of the instrument head 2 so that the tool 4 protrudes out of the instrument head 2 at an angle to the handle part 25 or its longitudinal axis. A pushbutton 27 is provided on the end of the instrument head 2 opposite the tool opening 26, cooperating with a tool release device 29 arranged in the instrument head 2 to release the tool 4 from the instrument head 2 or the tool-holding device 28. The instrument 1 may of course also have other known forms, for example, a pistol shape or it may be straight.

For example, there may be a device for transmitting working energy to the tool-holding device 28, in particular a shaft or a fluid line, one or more fluid or media lines 32, for example, one or more media lines for (cooling) water or (cooling) compressed air, optical fibres and/or electric power supply lines or control lines extending through the instrument 1 from the connecting device 24. According to FIG. 9, a fluid line 30 conveys a drive fluid, for example, compressed air to a drive unit in the form of a rotatable rotation part 31, in particular a rotor. The rotation part 31 is connected to the tool-holding device 28 to induce movement to the tool-holding device 28 and to a tool 4 accommodated therein.

A lighting device 3, 3A is provided on the instrument head 2, in particular on the end of the instrument head 2 with the tool opening 26. The lighting device 3, 3A is in particular arranged around the tool opening 26, surrounding it annularly so that the lighting device 3, 3A is designed as a ring light.

Figure 2:
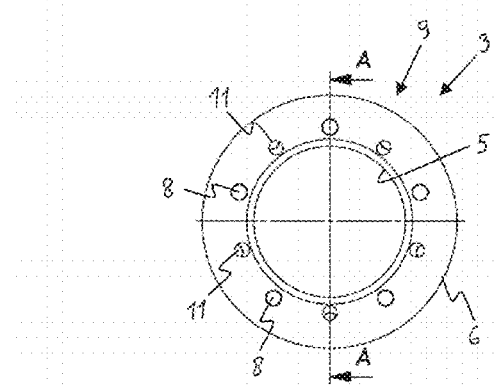
FIG. 2 shows an embodiment of a radiation-emitting end of a lighting device having at least one semiconductor element, wherein the radiation-emitting end has a plurality of radiation-emitting surfaces and a plurality of openings for dispensing fluid.
Figures 3, 4:
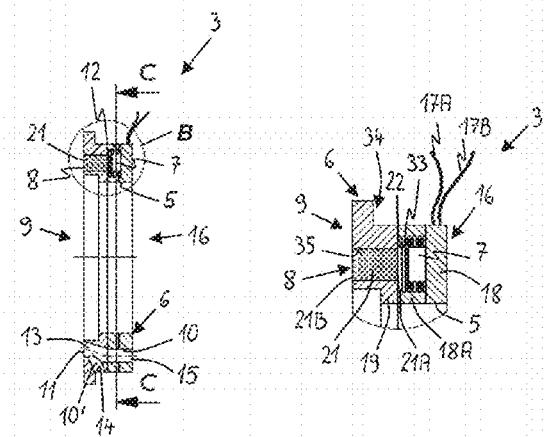
FIG. 3 shows a cross section through the lighting device from FIG. 2 along line A-A.
FIG. 4 shows the section labelled as B in FIG. 3 on an enlarged scale with a semiconductor element and an optical conductor allocated to the semiconductor element.

FIGS. 2 through 4 show an embodiment of a lighting device 3. The lighting device 3 has a radiation-emitting end 9 and an instrument-connecting end 16 arranged essentially parallel to the former. From the radiation-emitting end 9 the lighting device 3 emits electromagnetic radiation, in particular visible electromagnetic radiation. The instrument-connecting end 16 serves to connect or attach the lighting device 3 to the instrument 1. A body 6 of the lighting device 3 with a (exterior) lateral surface 12 extends between the two ends 9, 16. The lateral surface 12 thus connects the two ends 9, 16. The lateral surface 12 is self-contained or has a closed outer circumference, including, e.g., a cylindrical or polygonal circumference.

The body 6 of the lighting device 3 has a, in particular central, borehole or receptacle or opening 5. The opening 5 is connected in alignment with the tool opening 26 or surrounds the tool opening 26. The tool 4 can be accommodated in the receptacle or opening 5 or the tool 4 can be introduced into or released from the instrument head 2 through the receptacle or opening 5. As shown in FIG. 2, the borehole or opening 5 can be cylindrical in design.

A semiconductor element 7 provided in or on the body 6 is designed for emission of electromagnetic radiation, in particular visible radiation (light). The semiconductor element 7 is designed, for example, as a light-emitting diode (LED) or as dies. At least a portion of the radiation generated by the semiconductor element 7 is emitted through one or more optically-conducting, in particular transparent, light- or radiation-emitting surfaces 8 on the radiation-emitting end 9 of the lighting device 3 or on a surface of the lighting device 3.

In addition, at least one fluid channel 10, 10' is provided in the body 6 of the lighting device 3, running from the radiation-emitting end 9 or the surface with the radiation-emitting surface 8 through at least a portion of the lighting device 3. The fluid channel 10, 10' ends with an opening 11 for dispensing fluid at the radiation-emitting end 9 or the surface with the light- or radiation-emitting surface 8. The at least one fluid channel 10, 10' is connected to the fluid line 32 (see FIG. 9) and is designed to conduct at least one fluid from the fluid line 32 through the lighting device 3 to the opening 11. The fluid is dispensed from the opening 11 to the surroundings, for example, to the treatment site and/or the tool 4.

The at least one fluid channel 10, 10', the at least one semiconductor element 7, the opening 11 and the light- or radiation-emitting surface 8 are arranged inside the self-contained (outer) lateral surface 12 of the body 6 or of the self-contained exterior circumference of the lateral surface 12.

The embodiment according to FIG. 2 shows a radiation-emitting end 9 of a lighting device 3 having a plurality of openings 11 for dispensing fluid and light- or radiation-emitting surfaces 8, in particular five openings 11 and surfaces 8. The openings 11 and the radiation-emitting surfaces 8 are arranged in alternation. One radiation-emitting surface 8 is provided between two openings 11 or one opening 11 is provided between two radiation-emitting surfaces 8. The openings 11 and the radiation-emitting surfaces 8 surround the receptacle or opening 5 essentially in a circle. The openings 11 are positioned somewhat closer to the receptacle or opening 5 than the radiation-emitting surfaces 8. The openings 11 and the radiation-emitting surfaces 8 are spaced a distance apart from one another. The sections or surfaces of the radiation-emitting end 9 between the openings 11 and the radiation-emitting surfaces 8 are not designed to dispense fluid and/or emit radiation, in particular these sections are essentially not optically-conducting or they are not transparent for visible light. These sections are manufactured from metal, in particular steel, for example. However, a different number and/or arrangement of the openings 11 and/or the radiation-emitting surfaces 8 is of course also possible.

It can be seen from FIG. 3 that the lighting device 3 has at least two fluid channels 10, 10'. These two fluid channels 10, 10' are preferably connected to different fluid lines 32 of the instrument 1, in particular to different fluid sources, for example, to a water source and a compressed air source. The fluid channel 10' has an opening 14 for connection to a fluid source on the (outer) lateral surface 12 of the body 6, while the fluid channel 10 has an opening 15 for connection to a fluid source on the instrument-connecting end 16 of the body 6.

The two fluid channels 10, 10' are preferably combined to form a fluid mixing chamber 13 or they open into a fluid mixing chamber 13, in which the fluids from the two fluid channels 10, 10' are combined. The fluid mixing chamber 13 and also the two fluid channels 10, 10' through the fluid mixing chamber 13 are connected to at least one opening 11 for dispensing fluid through which the two preferably mixed fluids or the fluid mixture are dispensed from the lighting device 3, in particular from its radiation-emitting end 9.

It can be seen from FIG. 4 in particular that the at least one semiconductor element 7 is accommodated in a chamber 22, in particular one that is hermetically sealed. When there are multiple semiconductor elements, then there are preferably also multiple separate chambers 22, in particular only one semiconductor element 7 being accommodated in each chamber 22 (see FIG. 5). The chamber 22 protects the semiconductor element 7 from contamination, in particular from particles or liquid, gaseous or vapour impurities.

The chamber 22 is arranged inside the (outer) lateral surface 12 of the body 6. The chamber 22 or the inside walls of the chamber 22 are preferably formed on multiple layers 18, 19, of which the body 6 of the lighting device 3 is made.

In addition to the semiconductor element 7, preferably at least one additional component is provided in the chamber 22. As shown in FIG. 4 in particular, the additional component comprises an element 33 for converting the wavelength of the radiation emitted by the semiconductor element, in particular for converting it into white light, for example, a converter, in particular a conversion film or a conversion paste. Such converters may contain colour conversion materials, for example, luminescent dyes, which are excited by blue light to light up in particular, thereby emitting a longer wavelength yellow light. Since not all of the blue light is converted, the resulting additive mixture of spectral colours yields white light. Orthosilicates or YAG dyes, for example, may be used as colour conversion materials, wherein the colour conversion pigments may in particular be embedded in an organic carrier material, preferably transparent epoxy resin or silicone-based carrier materials.

The lighting device 3 additionally has a least one optical radiation conductor 21, which is arranged in such a way that it conducts electromagnetic radiation emitted by the semiconductor element 7 in the direction of the radiation-emitting end 9 and/or the light- or radiation-emitting surface 8 of the lighting device 3. If multiple semiconductor elements are provided, then multiple radiation conductors 21 may also be present, preferably each semiconductor element 7 is provided with its own radiation conductor 21. The radiation conductor 21 has two ends 21A, 21B, a first end 21A facing a semiconductor element 7. The first end 21A may be connected to the chamber 22 or may form part of the border of the chamber 22, in particular a part of the bordering wall of the chamber 22. The second end 21B of the radiation conductor 21 points in the direction of the radiation-emitting end 9 or forms at least a portion of the light- or radiation-emitting surface 8 of the lighting device 3. The radiation conductor 21 is designed, for example, as a cylinder, a rod (see FIG. 4) or a flat disk (see FIG. 6). The radiation conductor 21 is in particular accommodated in a borehole in the lighting device 3 or in a layer 18, 19 of the lighting device 3, for example, by fusing it in place there. The radiation conductor 21 is designed, for example, as a glass, a glass fibre bundle, a synthetic resin or a plastic element.

The FIGS. 3, 4, 6 and 7 in particular show that the lighting devices 3, 3A and 3B or the body 6 consist of multiple layers 18, 19. The layers 18, 19 are joined to one another fixedly, for example, by welding, soldering, melting or gluing.

The lighting device 3 of FIGS. 3 and 4 has a first ceramic layer 18 in which preferably the electric conductor 17 (see FIG. 5) is also arranged for electrically supplying the at least one semiconductor element 7. The electric contacts 17A, 17B, which connect the electric conductor 17 to an electric power source, are preferably also provided on the ceramic layer 18. The ceramic layer 18 is round or circular or ring-shaped, for example.

A second ceramic layer 18A, in which at least one borehole forming at least part of the chamber 22 is provided, is connected to the ceramic layer 18. The wall of the borehole thus forms part of the inside wall of the chamber 22. This is connected to a third metallic layer 19. At least one element 34 for applying or attaching the lighting device 3 to the instrument head 2 is preferably provided on this metallic layer 19, for example, a stop, a protrusion, an undercut, a projection, a thread or the like. The metallic layer 19 also forms the radiation-emitting end 9 or the surface of the lighting device 3 on which the light- or radiation-emitting surfaces 8 are situated.

The three layers 18, 18A and 19 are in particular not designed to conduct visible light, i.e., they are not transparent. Therefore at least one optical radiation conductor 21, which is already described above, is provided for conducting the electromagnetic radiation, in particular the visible light generated by the at least one semiconductor element 7. To accommodate this radiation conductor 21, at least one of the layers 18, 18A, 19 has a borehole 35 (for example, layer 19 according to FIG. 4), which extends in particular from the radiation-emitting end 9 or a surface of the lighting device 3 to the chamber 22.

Figure 5:
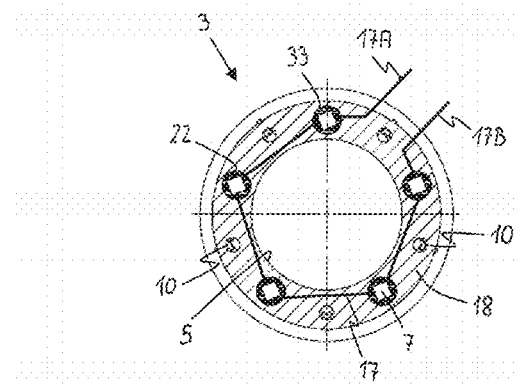
FIG. 5 shows a longitudinal section through the lighting device of FIG. 3 along line C-C as well as the electric power supply to the semiconductor elements.

FIG. 5 shows in a view from above the course of the conductor 17 for supplying electric power to the semiconductor elements 7 in the ceramic layer 18. It can be seen here that the semiconductor elements 7 are connected in series and are connected through the electric conductor 17. The electric conductor 17 is additionally arranged at a distance from the fluid channel 10. Because of the electric insulation in the form of the ceramic layer 18, the conductor 17 does not require an electrically insulating outer jacket or exterior electrical insulation.

Figure 6:
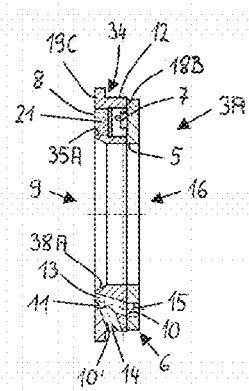
FIG. 6 shows a cross section through an alternative embodiment of a lighting device having at least one semiconductor element and at least one opening for dispensing fluid.
Figure 7:
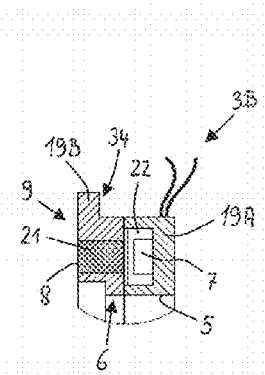
FIG. 7 shows another embodiment of a chamber of a lighting device having a semiconductor element and an optical conductor allocated to the semiconductor element.

The lighting devices 3A and 3B of FIGS. 6 and 7 resemble in design the lighting device 3 of FIGS. 2-5, wherein the same components are labelled with the same reference numerals to avoid repetition.

In deviation from the lighting device 3, the lighting device 3A of FIG. 6 comprises only two layers 18B and 19C. The layer 18B is formed by a ceramic material. The layer 18B is preferably in the form of a ceramic ring. A metallic layer 19C is connected to the layer 18B. The layer 19C, which is also essentially ring-shaped, has at least one borehole 35A, in which the radiation conductor 21 can be accommodated. Preferably at least a part of the borehole 35A also forms at least a part of the chamber 22 or the at least one semiconductor element 7 and/or the converter element 33 are accommodated in the borehole 35A.

The lighting device 3B in FIG. 7 also consists of only two layers 19A, 19B. These layers 19A, 19B are preferably both made of metal. The electric conductor 17 arranged in the layer 19A is thus equipped with an electric insulation accordingly. A borehole is again provided for the radiation conductor 21 in at least one of the two layers 19A, 19B. A receptacle for the at least one semiconductor element 7 or a borehole forming at least a part of the chamber 22 is arranged in at least one of the two layers 19A, 19B.

FIG. 8 shows a lighting device 3C, the design of which corresponds essentially to the lighting device 3, 3A, 3B described above so that to avoid repetition the same components are again provided with the same reference numerals. However, the radiation-emitting end 9 of the lighting device 3C only has a single transparent light- or radiation-emitting surface 8, transparent for visible light in particular, and which is designed substantially in a ring shape or extends around the opening 5. The radiation-emitting end 9 or the radiation-emitting surface 8 is preferably formed by a plastic, synthetic resin or glass layer 20. The layer 20 extends either up to the at least one semiconductor element 7, which thus emits electromagnetic radiation, in particular visible light, directly to the layer 20, or there is at least one optical radiation conductor, in particular a radiation conductor 21, such as that described above, provided between the layer 20 and the at least one semiconductor element 7 to conduct the radiation to the layer 20.

In addition, the openings 11 are provided in the layer 20 for dispensing fluid. The openings 11 are thus separated from one another by radiation-emitting sections of the radiation-emitting surface 8 that are transparent, in particular for visible light.

The lighting device 3D of FIG. 10 differs from the lighting devices described above in particular in that a ring-shaped channel 40 is provided on its (outer) lateral surface 12. The ring channel 40 is designed to accommodate a fluid, in particular water, and is or can be connected to a fluid source, preferably through lines and/or channels in the instrument 1. The ring channel 40 is connected to the fluid-dispensing opening 11 and/or to the mixing chamber 13, in particular through the fluid channel 10'. Such a ring channel 40 may also be provided in the lighting devices 3, 3A, 3B or 3C.

The lighting device 3D additionally comprises two layers, wherein preferably the layer 18B is made of ceramic and the layer 19C is made of metal. The ring channel 40 is provided in the layer 19C. The layer 19C has a flange 41 and/or a shoulder 42 for connecting or supporting the layer 18B. The shoulder 42 and the ring channel 40 are preferably arranged on different or opposing sides of the lighting device 3D. At least one optical radiation conductor 21 is accommodated in at least one borehole in the layer 19C.

FIG. 9 shows a sectional diagram through an instrument head 2 of an instrument 1 with a lighting device 3A according to FIG. 6 (however, the lighting devices 3, 3B, 3C, 3D may of course be implemented accordingly in the instrument head 2). The lighting device 3A is arranged, preferably detachably, in a receptacle 36, which is circular or ring-shaped in particular, or in an undercut in the instrument head 2. A threaded sleeve 37 which can be connected to a threaded component of the instrument 1 and which secures the lighting device 3A in the receptacle 36, for example, by clamping it there, is provided as a fastening element for the lighting device 3A. To do so, contact faces 38A, 38B are provided on the threaded sleeve 37 and on the lighting device 3A. The threaded sleeve 37 is preferably designed so that it can be accommodated in the opening 5 of the lighting device 3A. The threaded sleeve 37 is preferably of such dimensions that at least a portion of the tool-holding device 28 can be accommodated in the internal bore in the threaded sleeve 37.

The receptacle 36 also serves as a connection between the media line or fluid line 32 and the at least one fluid channel 10 or as a line segment, which conducts fluid from the media line or fluid line 32 to the at least one fluid channel 10. The receptacle 36 is designed in particular at least as part of a channel, for example, in a ring shape or as a ring channel which dispenses a fluid to multiple fluid channels 10, 10'. A sealing element 39, for example, an O-ring, is preferably provided in the receptacle 36.

Finally, FIG. 9 shows a control and/or supply device 23 which is connected to the instrument 1 by the connecting device 24. The control and/or power supply device 23 supplies media, in particular fluids, electric power and/or control signals to the instrument 1 through a supply tubing and/or it controls or monitors the operation of the instrument 1. The control and/or supply device 23 thus also provides the electric power for the at least one semiconductor element 7 and the at least one fluid which can be dispensed through the lighting device 3A.

The control and/or supply device 23 is preferably designed to control an alternating emission of the electromagnetic radiation and dispensing of the fluid from the light- or radiation-emitting end 9 of the lighting device 3A. This is done, for example, through corresponding electric control signals to the semiconductor element 7, in particular through a pulsed supply of electric power to the semiconductor element 7 and by opening and closing a control element, for example, a valve in a media line or fluid line 32 connected to the opening 11 for dispensing fluid.

FIG. 11 shows a sectional diagram through an instrument head 2 of an instrument 1 with a lighting device 3D according to FIG. 10 (however, the lighting devices 3, 3A, 3B, 3C can of course also be implemented in the instrument head 2 accordingly). The same components illustrated in FIGS. 9 and 11 carry the same reference numerals.

The lighting device 3D is undetachably connected to the instrument head 2, preferably by press fitting the lighting device 3D to the instrument head 2, in particular by pressing the lighting device 3D into the receptacle 36, or by a force-fit connection or a frictional connection between the lighting device 3D and the instrument head 2, in particular the receptacle 36.

To optionally be able to exchange the lighting device 3D, in a preferred embodiment it is provided that the instrument head 2 together with the lighting device 3 is detachable from the instrument 1, in particular from the handle part 25. The instrument head 2 therefore has a coupling element 43 which can be connected to a corresponding coupling element of the handle part 25 and forms a coupling device. At least one fluid or media line 30, 32, 44 is provided on the coupling element 43, in particular for air or water, said media line being connectable to at least one corresponding line in the handle part 25 or to its coupling element, preferably by means of plugs. In addition, an electric connecting device 45 is provided on the coupling element 43, in particular two electric contacts which can be connected to a corresponding electric connecting device on the coupling element of the handle part 25. Through this electric connecting device, the lighting device 3D, in particular the at least one semiconductor element 7 can be connected to an electric power source and supplied with electric power.

The instruments 1 illustrated in FIGS. 9 and 11 are designed as compressed-air-operated instruments with an impeller 31. Of course it is possible accordingly to implement a lighting device 3-3G in an instrument with a mechanical drive of the tool 4, wherein the mechanical drive comprises as least one shaft which transmits a drive movement to the tool-holding device 28 and/or the tool 4.

FIG. 12 shows a lighting device 3E, whose body 6 is manufactured at least partially or completely from casting material or injection-moulded material, for example, synthetic resin, in particular epoxy resin or a thermoplastic resin, for example, random propylene copolymers (PPR), polycarbonate (PC), polymethylenepentene (PMP), cycloolefin copolymers (COC) or polyphenylsulfone (PPSU). The at least one semiconductor element 7 and/or the at least one fluid channel 10, 10', 40 and/or the at least one electric conductor 17 and/or the chamber 22 and/or the optical radiation conductor 21 is/are preferably embedded in the casting material or the injection-moulded material or at least partially surrounded by it. Moreover the lighting device 3E corresponds essentially to the lighting devices 3-3D described above.

With the lighting devices 3-3E illustrated in FIGS. 1-12, the body 6 is designed as a closed ring or as a hollow cylinder. However, it is of course also possible to design the lighting device with two free ends or end faces 46A, 46B, in particular with a curve or curve shape or as an arc of a circle as exemplified by the lighting device 3F in FIG. 13. A clearance or an opening is provided between the free ends 46A, 46B. Otherwise the lighting device 3F again corresponds essentially to the lighting devices 3-3E described above. There is of course also the possibility of designing an angular lighting device with a closed angular shape or an angular shape with free ends.

FIG. 14 shows a lighting device 3G whose body 6 consists of two parts 6A, 6B, the radiation-emitting end 9 and/or the at least one radiation-emitting surface 8 being provided on one part 6A, and the at least one opening 11 for dispensing fluid being provided on the other part 6B. The at least one semiconductor element 7 and/or the at least one electric conductor 17 and/or the chamber 22 and/or the optical radiation conductor 21 is/are preferably provided on one of the two parts 6A, 6B, in particular on the part 6A having the radiation-emitting end 9 and/or the at least one radiation-emitting surface 8. Alternatively or additionally, the at least one fluid channel 10, 10', 40 is preferably provided on one of the two parts 6A, 6B, in particular on the part 6B with the at least one opening 11 for dispensing fluid. One part 6A, 6B preferably surrounds the other part 6A, 6B. The two parts 6A, 6B are preferably arranged concentrically. The two parts 6A, 6B are preferably inseparably attached to one another. The two parts 6A, 6B are preferably manufactured from the same material or different materials. Moreover the lighting device 3G corresponds essentially to the lighting devices 3-3F described above.

FIGS. 15 and 16 show two embodiments of lighting devices 50, 50'. Because of their very similar structure, the following description applies to both FIGS. 15 and 16, wherein the same or similar components are provided with the same reference numerals. The lighting devices 50, 50' are preferably provided for fastening to an instrument or instrument head, in particular in or on an instrument 1 or an instrument head 2, as illustrated in FIGS. 1, 9 and 11 and as described in conjunction with those figures. Accordingly all the features of instruments 1 or instrument heads 2 described in conjunction with FIG. 1, 9 or 11 can also be applied to an instrument or an instrument head with a lighting device 50, 50'.

The lighting device 50, 50' comprises a hollow metallic sleeve 51, a transparent window 53 for emitting electromagnetic radiation, in particular visible light and a socket 54. An optical semiconductor element 55, which is provided on the socket 54, is designed to emit electromagnetic radiation, in particular visible light.

The hollow metallic sleeve 51 is designed in particular as a cylindrical sleeve or a hollow cylinder with a through-bore 52. The through-bore 52 forms a round or circular opening 65 at one end of the sleeve 51. At one end of the sleeve 51 or the through-bore 52, the transparent window 53 is provided in the opening 65, with complementary shoulders or protrusions or flanges 63, 64 being provided on the sleeve 51 and the window 53 so that the window 53 is supported on the sleeve 51. The transparent window 53 is preferably fused in the hollow metallic sleeve 51. The transparent window 53 preferably comprises a convex shape, for example, a lenticular shape, for concentrating the electromagnetic radiation emitted by the optical semiconductor element 55.

On the end of the sleeve 51 opposite the opening 65 the through-bore 52 forms another opening, in particular a round or circular opening. The socket 54 provided in or on this opening is made of a ceramic material or a glass ceramic material or glass. The socket 54 is designed to be round or flat or essentially plate-shaped and comprises an outer jacket, a top side and a bottom side arranged essentially parallel to the top side. The transparent window 53 and the socket 54 close or cap the through-bore 52 or the openings 65 in the hollow metallic sleeve 51 in such a way as to form a chamber 56 in which the at least one optical semiconductor element 55 is accommodated. The optical semiconductor element 55 is attached to the socket 54, in particular to the top side of the socket 54 pointing into the interior of the chamber 56.

The socket 54 has a plurality of electric contacts for electrical connection of the optical semiconductor element 55 to an electric power source. Two electric contacts, preferably pin-shaped or line-type contacts 58 are accommodated in boreholes 62 in the socket 54 or they pass through the socket 55 in particular in such a way that the contacts 58 end on different surfaces of the socket 54, for example, on its top side and its bottom side. Two additional electric contacts or surface contacts 59, 60 are provided on surfaces of the socket 54, in particular on its top side and on its bottom side. The at least one optical semiconductor element 55 is connected directly or indirectly to one or more of the contacts 58, 59, 60, the at least one optical semiconductor element 55 preferably being arranged on at least one of the surface contacts 59. The electric contacts 58, 59, 60 are electrically connected to one another and are part of a switch circuit or current circuit that is or can be connected to an electric power source.

As shown in conjunction with FIG. 17 in particular, two surface contacts 59 which form an electric positive pole and a negative pole, for example, along with the at least one optical semiconductor element 55 are arranged on the top side of the socket 54. The top ends of the two electric contacts 58, each of which is electrically connected to one of the surface contacts 59, are also indicated in FIG. 17. The two surface contacts 60 which form an electric positive pole and a negative pole, for example, are arranged on the bottom side of the socket 54 (see also FIG. 18). The bottom side of the socket 54 with the two surface contacts 60 preferably also forms an exterior of the lighting device 50, 50'. For the purpose of correct mounting, in particular of a correct electric contacting of the at least one optical semiconductor element 55, a mark 67 may be provided on at least one electric contact 58, 59, 60; for example, a contact 58, 59, 60 may be shaped differently or an alphanumeric character may be provided.

The electric contacts 58, 59, 60 comprise a material comprising metal and glass, in particular a metal- and glass-particle-containing mixture whose particles are connected or bonded or fused to one another and to the socket 54 by heating, in particular sintering. The material comprising metal and glass is applied to the socket 54 and/or is introduced into a borehole 62 in the socket 54, preferably prior to the heating or sintering. In particular the surface contacts 59, 60 have at least one additional electrically conducting layer, for example, a gold-containing layer or alloy. This additional electrically conducting layer is applied to the material comprising metal and glass, in particular after heating or sintering the socket 54 and/or the material comprising metal and glass.

The differences in the lighting devices 50, 50' illustrated in FIGS. 15 and 16 are described below:

Referring to the lighting device 50 of FIG. 15 the connection between the socket 54 and the hollow metallic sleeve 51 or the material connecting the socket 54 and the sleeve 51 comprises a material 57 which comprises metal and glass, in particular a mixture consisting of metal and glass particles, in which the particles are bonded or fused to one another and to the socket 54 and/or the sleeve 51 by heating, in particular by sintering the socket 54. The material 57 comprising metal and glass for connecting the socket 54 to the sleeve 51 is preferably the same as the material comprising metal and glass of the electric contacts 58, 59, 60 and/or is applied jointly to the socket 54 and optionally to the sleeve 51 within one process step, preferably prior to heating or sintering.

The connection between the socket 54 and the hollow metallic sleeve 51 or the material connecting the socket 54 and the sleeve 51 additionally comprises a metal alloy 61, for example, a metal solder. The metal alloy is applied to the material 57 comprising metal and glass which serves as a backing or an adhesion promoter, preferably applying it after heating or sintering the material 57 comprising metal and glass. The connection between the socket 54 and the hollow metallic sleeve 51 thus comprises multiple materials or components which are formed as layers in particular or are applied one after the other (see also FIG. 19).

In the lighting device 50' of FIG. 16, the connection between the socket 54 and the hollow metallic sleeve 51 or the material connecting the socket 54 and the sleeve 51 comprises a casting material or adhesive material 71, for example, a silicone or epoxy resin or a silicone or epoxy adhesive. According to one embodiment, the casting material or adhesive material 71 is provided between the contact area of the socket 54 and the sleeve 51 or in a connecting area the width of which corresponds essentially to the wall thickness of the wall 66. Alternatively or additionally, the casting or adhesive material 71 is also provided on the outside of the socket 54, for example, on a flange 68 and/or on the outside of the sleeve 51, for example, on a flange 69. Alternatively or additionally, the casting material or adhesive material 71 is provided in the interior of the sleeve 51 and/or in the chamber 56. The casting material or adhesive material 71 especially preferably covers or surrounds at least one side or surface of the optical semiconductor element 55, optionally multiple sides or surfaces of the optical semiconductor element 55 including the side or surface facing the transparent window 53 and thus in particular forms a protective layer for the optical semiconductor element 55.

A combination of the two types of connection between the socket 54 and the hollow metallic sleeve 51 as described above is of course also possible, i.e., a connection which includes a material 57 comprising metal and glass and a casting material or adhesive material 71 and preferably also a metal alloy 61. In this embodiment, the material 57 comprising metal and glass and optionally the metal alloy 61 are provided in particular between the socket 54 and the sleeve 51 (as illustrated in FIGS. 15 and 19) or in the connecting area mentioned above and the casting material or adhesive material 71 is provided in the chamber 56 and/or on the outside of the lighting device.

In the lighting devices 50 of FIG. 15, the sleeve 51 and the socket 54 have essentially the same outside diameter so that the outside diameter of the lighting devices 50 corresponds approximately to the outside diameter of the sleeve 51 and of the socket 54. To produce a tight, secure connection between the socket 54 and the sleeve 51, the wall thickness of the wall 66 of the sleeve 51 is substantially sufficient. In other words the connection between the socket 54 and the sleeve 51 is defined by a connecting area, the width of which corresponds essentially to the thickness of the wall 66. In contrast with that the diameter of the socket 54 of the lighting devices 50' in FIG. 16 is wider than the diameter of the sleeve 51 so that a flange 68 is formed, serving to fasten the lighting devices 50 on the instrument 1, for example. The sleeve 51 may optionally also have a widened area or a flange 69 on its end where it is connected to the socket 54 so that the connecting area between the socket 54 and the sleeve 51 is wider than the thickness of the wall 66 of the sleeve 51. A flange 68, 69 may of course also be provided on the lighting devices 50 of FIG. 15, or the lighting devices 50' of FIG. 16 may be designed without a flange, as shown in FIG. 15.

Another difference between the lighting devices 50 and 50' consists of the arrangement and/or design of the at least one optical semiconductor element 55. With the optical semiconductor element 55 of FIG. 15, the electric positive pole and the electric negative pole are positioned on different sides, in particular opposite sides of the optical semiconductor element 55. For connecting the positive pole and the negative pole to the electric contacts 58, 59, 60 it is provided that the optical semiconductor element 55 is arranged with one of the two poles directly on a first surface contact 59 on the top side of the socket 54 and to connect the other of the two poles to a second surface contact 60 on the top side of the socket 54 by means of an electric conductor 70, for example, by means of a wire, in particular by means of a gold wire. The optical semiconductor element 55 of the lighting devices 50' of FIG. 16 has both electric poles on the same side (so-called Flip-Chip), so that the optical semiconductor element 55 can be arranged with both poles directly on the two surface contacts 59 on the top side of the socket 54. It is of course also possible to provide a Flip-Chip in the lighting device 50 of FIG. 15 or an optical semiconductor element 55 with an electric conductor 70 in the lighting device 50' of FIG. 16.

The invention is not limited to the embodiments described here but instead includes all embodiments, which apply or comprise the basic function principle of the invention. In addition, all the features of all the embodiments described and illustrated here can be combined with one another. In particular according to one embodiment, the body of a lighting device in which at least one fluid channel and/or at least one opening for dispensing fluid is/are provided as illustrated in FIGS. 1-14 and as disclosed in the respective description referring to same, may have a socket made of a ceramic material or a glass ceramic material or glass which is connected to a hollow metallic sleeve by a material comprising metal and glass as illustrated in FIGS. 15-18 and as disclosed in the respective description or the description referring thereto.

What is claimed is:

1. A lighting device for an instrument head of a medical or dental instrument, wherein a tool for acting on a treatment site is provided on the instrument head, and wherein the lighting device comprises:
    a receptacle or an opening, in which the tool can be accommodated,
    an annular body surrounding the receptacle or opening,
    at least one semiconductor element sealed in the body and configured for emission of electromagnetic radiation,
    one or more optically-conducting radiation-emitting surfaces on a radiation-emitting end of the body, through which the electromagnetic radiation emitted by the at least one semiconductor element can be emitted by the lighting device, and
    at least one fluid channel, which is provided in the body of the lighting device and connects at least one opening for dispensing fluid on the radiation-emitting end of the lighting device to one or more fluid sources,
    wherein the body of the lighting device comprises a lateral surface extending from the radiation-emitting end, and
    wherein a ring-shaped channel is provided on the lateral surface which is designed to receive a fluid from the one or more fluid sources and is connected to the at least one opening for dispensing fluid via the at least one fluid channel.

2. The lighting device according to claim 1, wherein the lateral surface extending from the radiation-emitting end forms a self-contained exterior circumference within which the at least one fluid channel is arranged.

3. The lighting device according to claim 1, wherein the at least one fluid channel comprises a plurality of fluid channels which are provided in the body of the lighting device and which open into a shared fluid mixing chamber in the lighting device, wherein the fluid mixing chamber is connected to the at least one opening for dispensing fluid.

4. The lighting device according to claim 1, wherein the at least one fluid channel has an opening for connection to a fluid source on the lateral surface of the body of the lighting device.

5. The lighting device according to claim 4, wherein the opening for connection to a fluid source on the lateral surface of the body of the lighting device is arranged in the ring-shaped channel on the lateral surface of the lighting device.

6. The lighting device according to claim 1, comprising a plurality of optically-conducting radiation-emitting surfaces and wherein the at least one opening for dispensing fluid on the radiation-emitting end of the lighting device comprises a plurality of openings for dispensing fluid, wherein at least one radiation-emitting surface is arranged between two openings for dispensing fluid.

7. The lighting device according to claim 1, wherein the at least one semiconductor element comprises a plurality of electrically series-connected semiconductor elements which are connected through an electric conductor, wherein the electric conductor is arranged at a distance from the at least one fluid channel in the body of the lighting device.

8. The lighting device according to claim 1, wherein the lighting device comprises multiple layers of different materials.

9. The lighting device according to claim 8, wherein the multiple layers comprise a first layer in which the at least one semiconductor element or an electrical conductor for supplying the at least one semiconductor element with electric power is provided, and wherein the first layer comprises a ceramic material or plastic.

10. The lighting device according to claim 8, wherein one of the multiple layers forms the radiation-emitting end of the lighting device and comprises at least one of: a metallic material, a plastic, and a glass.

11. The lighting device according to claim 1, wherein the at least one semiconductor element comprises a plurality of semiconductor elements, further comprising a corresponding plurality of distinct optical radiation conductors assigned to the semiconductor elements, wherein each of the plurality of distinct optical radiation conductors is arranged to conduct the electromagnetic radiation emitted by a respective one of the semiconductor elements in a direction of the radiation-emitting end of the lighting device and wherein said distinct optical radiation conductors are spaced from one another by a region which does not emit any electromagnetic radiation.

12. The lighting device according to claim 1, wherein the at least one semiconductor element is arranged in a hermetically sealed chamber in the body of the lighting device.

13. The lighting device according to claim 1, further comprising a control unit that controls emission of the electromagnetic radiation from the semiconductor element to occur alternatingly with the dispensing of the fluid from the radiation-emitting end of the lighting device.

14. The lighting device according to claim 1, wherein the lighting device is detachably connectable to the medical or dental instrument or instrument head.

15. An instrument head of a medical or dental instrument, comprising a lighting device according to claim 1.

16. The lighting device according to claim 1, wherein the lighting device comprises a metallic portion in which the at least one fluid channel and/or the ring-shaped channel is/are arranged.

17. The lighting device according to claim 1, further comprising a converting element or conversion material sealed in the body and coupled to the at least one semiconductor element, and wherein the converting element or conversion material is configured to convert light emitted by the semiconductor element from a first wavelength into a predetermined second wavelength.

18. A lighting device for an instrument head of a medical or dental instrument, wherein a tool for acting on a treatment site is provided on the instrument head, and wherein the lighting device comprises:
    a receptacle or an opening in which the tool can be accommodated,
    a body surrounding the receptacle or opening,
    at least one semiconductor element provided in or on the body, designed for emission of electromagnetic radiation,
    one or more optically-conducting radiation-emitting surfaces provided on the body of the lighting device, through which the electromagnetic radiation emitted by the at least one semiconductor element can be emitted by the lighting device, and a plurality of openings for dispensing fluid provided on the body of the lighting device, wherein
at least one opening of the plurality of openings for dispensing fluid and the one or more optically-conducting radiation-emitting surfaces are spaced apart by a region which does not emit any electromagnetic radiation and does not dispense any fluid, wherein said region is a portion of the body of the lighting device.

19. The lighting device according to claim 18, wherein the body of the lighting device comprises a lateral surface extending from a surface of the body having the plurality of openings for dispensing fluid, said lateral surface forming a self-contained exterior circumference within which the one or more optically-conducting radiation-emitting surfaces and the openings for dispensing fluid are arranged.

20. The lighting device according to claim 18, comprising at least one fluid channel within the body of the lighting device, said fluid channel connecting the openings for dispensing fluid to one or more fluid sources.

21. The lighting device according to claim 20, wherein the at least one fluid channel comprises a plurality of fluid channels which open into at least one shared fluid mixing chamber in the lighting device, wherein the at least one fluid mixing chamber is connected to the openings for dispensing fluid.

22. The lighting device according to claim 20, wherein the at least one fluid channel has an opening for connection to a fluid source on a lateral surface of the body of the lighting device.

23. The lighting device according to claim 20, wherein the at least one semiconductor element comprises a plurality of electrically series-connected semiconductor elements which are connected through an electric conductor, and wherein the electric conductor is spaced a distance from the at least one fluid channel.

24. The lighting device according to claim 18, wherein the lighting device comprises multiple layers of different materials.

25. The lighting device according to claim 24, wherein the multiple layers comprise a first layer in which the at least one semiconductor element or an electrical conductor for supplying the at least one semiconductor element with electric power is provided, and wherein the first layer comprises a ceramic material or plastic.

26. The lighting device according to claim 24, wherein one of the multiple layers that forms the radiation-emitting end of the lighting device comprises at least one of: a metallic material, a plastic, and a glass.

27. The lighting device according to claim 18, wherein the at least one semiconductor element comprises a plurality of semiconductor elements, further comprising a corresponding plurality of optical radiation conductors assigned to the plurality of semiconductor elements, wherein each of the plurality of conductors is arranged to conduct the electromagnetic radiation emitted by a respective one of the semiconductor elements in the direction of the one or more optically-conducting radiation-emitting surfaces.

28. The lighting device according to claim 18, wherein the at least one semiconductor element is arranged in a hermetically sealed chamber in the body of the lighting device.

29. The lighting device according to claim 18, further comprising a control unit that controls emission of the electromagnetic radiation from the semiconductor element to occur alternatingly with the dispensing of the fluid from the at least one radiation-emitting surface of the lighting device.

30. The lighting device according to claim 18, wherein the openings for dispensing fluid and the one or more optically-conducting radiation-emitting surfaces are arranged essentially in a ring pattern around the receptacle or the opening of the lighting device.

31. The lighting device according to claim 18, wherein the lighting device is detachably connectable to the medical or dental instrument or instrument head.

32. An instrument head of a medical or dental instrument comprising a lighting device according to claim 18.

33. A lighting device for an instrument head of a medical or dental instrument, wherein a tool for acting on a treatment site is provided on the instrument head, and wherein the lighting device comprises:
a receptacle or an opening in which the tool can be accommodated,
a body surrounding the receptacle or opening which has a radiation-emitting end with at least one optically-conducting radiation-emitting surface, an instrument-connecting end and a lateral surface extending between the radiation-emitting end and the instrument-connecting end,
at least one semiconductor element which is provided in or on the body and is designed for emission of electromagnetic radiation so that electromagnetic radiation can be emitted by the at least one optically-conducting radiation-emitting surface of the radiation-emitting end, and
at least one opening provided on the radiation-emitting end of the body of the lighting device for dispensing fluid so that at least one fluid or a fluid mixture can be dispensed from the radiation-emitting end of the body, wherein
the radiation-emitting end of the body comprises a metallic layer and the at least one radiation-emitting surface comprises glass which is fused in the metallic layer.

34. The lighting device according to claim 33, wherein the lateral surface of the body of the lighting device forms a closed exterior circumference within which the at least one optically-conducting radiation-emitting surface and the at least one opening for dispensing fluid are arranged.

35. The lighting device according to claim 33, further comprising at least one fluid channel provided in the body of the lighting device to connect the at least one opening on the radiation-emitting end of the lighting device to one or more fluid sources for dispensing fluid.

36. The lighting device according to claim 33, further comprising at least one shared fluid mixing chamber defined in the lighting device and a plurality of fluid channels provided in the lighting device, wherein the plurality of fluid channels open into the at least one shared fluid mixing chamber in the lighting device, and wherein the at least one fluid mixing chamber is connected to the at least one opening for dispensing fluid.

37. The lighting device according to claim 33, further comprising a plurality of fluid channels provided in the lighting device, wherein at least a first of the plurality of fluid channels has an opening for connection to a fluid source on the lateral surface of the body of the lighting device, and wherein at least a second of the plurality of fluid channels has an opening for connection to a fluid source on an instrument-connecting end of the body of the lighting device.

38. The lighting device according to claim 33, wherein the at least one optically-conducting radiation-emitting surface comprises a plurality of optically-conducting radiation-emitting surfaces and the at least one opening for dispensing fluid comprises a plurality of openings for dispensing fluid, wherein at least one radiation-emitting surface of the plurality of radiation-emitting surface is arranged between two openings of the plurality of openings for dispensing fluid.

39. The lighting device according to claim 33, wherein the at least one semiconductor element comprises a plurality of electrically series-connected semiconductor elements which are connected through an electric conductor, wherein the electric conductor is arranged at a distance from the at least one fluid channel provided in the lighting device.

40. The lighting device according to claim 33, wherein the lighting device comprises multiple layers of different materials.

41. The lighting device according to claim 40, wherein the multiple layers comprise a first layer in which the at least one semiconductor element or an electrical conductor for supplying the at least one semiconductor element with electric power is provided, and wherein the first layer comprises a ceramic material or plastic.

42. The lighting device according to claim 40, wherein the layer that forms the radiation-emitting end of the lighting device comprises at least one of a plastic or a glass.

43. The lighting device according to claim 33, wherein the at least one semiconductor element comprises a plurality of semiconductor elements, further comprising a corresponding plurality of optical radiation conductors assigned to the plurality of semiconductor elements, wherein each of the plurality of conductors is arranged to conduct the electromagnetic radiation emitted by a respective one of the plurality of semiconductor elements in a direction of the radiation-emitting end of the lighting device.

44. The lighting device according to claim 33, wherein the at least one semiconductor element is arranged in a hermetically sealed chamber in the body of the lighting device.

45. The lighting device according to claim 33, further comprising a control unit that controls emission of the electromagnetic radiation from the semiconductor element to occur alternatingly with the dispensing of the fluid from the radiation-emitting end of the lighting device.

46. The lighting device according to claim 33, wherein the lighting device is detachably connectable to the medical or dental instrument or instrument head.

47. An instrument head of a medical or dental instrument, comprising a lighting device according to claim 33.

48. The lighting device according to claim 33, further comprising at least one optical radiation conductor which comprises the at least one optically-conducting radiation-emitting surface and is arranged to conduct the electromagnetic radiation emitted by the at least one semiconductor element in a direction of the radiation-emitting end of the lighting device.

49. A lighting device for an instrument head of a medical or dental instrument, wherein a tool for acting on a treatment site is provided on the instrument head, and wherein the lighting device comprises:
a receptacle or an opening, in which the tool can be accommodated,
a body surrounding the receptacle or opening,
at least one semiconductor element provided in or on the body, designed for emission of electromagnetic radiation,
one or more optically-conducting radiation-emitting surfaces on a radiation-emitting end of the body of the lighting device, through which the electromagnetic radiation emitted by the at least one semiconductor element can be emitted by the lighting device, and
at least one fluid channel, which is provided in the body of the lighting device and connects at least one opening for dispensing fluid on the radiation-emitting end of the lighting device to one or more fluid sources, wherein
the body of the lighting device comprises a metallic portion made of metal, wherein the metallic portion comprises a flange and/or a shoulder for supporting a ceramic portion comprising ceramic on which the at least one semiconductor element is provided, such that the metallic portion and the ceramic portion form a hermetically sealed chamber in which the at least one semiconductor element is arranged.

50. The lighting device according to claim 49, further comprising a ring channel provided on a lateral surface of the metallic portion of the body, wherein the ring channel is designed to receive a fluid and is connected through the at least one fluid channel to the at least one fluid-dispensing opening.

51. The lighting device according to claim 49, wherein the at least one radiation-emitting surface comprises glass and is arranged or fused in the metallic portion.

52. The lighting device according to claim 49, wherein the at least one opening for dispensing fluid and the one or more optically-conducting radiation-emitting surfaces are spaced apart by a region which does not emit any electromagnetic radiation and does not dispense any fluid.

53. The lighting device according to claim 49, wherein the metallic portion made of metal comprises the radiation-emitting end of the lighting device.

54. An instrument head of a medical or dental instrument, comprising a lighting device according to claim 49.

* * * * *